(12) United States Patent
Bartels

(10) Patent No.: US 10,322,632 B2
(45) Date of Patent: Jun. 18, 2019

(54) METHOD FOR CONTROLLING A FUNCTIONAL COMPONENT OF A TRANSPORTATION VEHICLE BY A MEDICAL IMPLANT OF A USER OF THE TRANSPORTATION VEHICLE, COMPUTER PROGRAM, CONTROL DEVICE FOR A TRANSPORTATION VEHICLE, AND MEDICAL IMPLANT

(71) Applicant: VOLKSWAGEN AKTIENGESELLSCHAFT, Wolfsburg (DE)

(72) Inventor: Bastian Bartels, Wolfsburg (DE)

(73) Assignee: VOLKSWAGEN AKTIENGESELLSCHAFT (DE)

( * ) Notice: Subject to any disclaimer, the term of this patent is extended or adjusted under 35 U.S.C. 154(b) by 0 days.

(21) Appl. No.: 16/060,313

(22) PCT Filed: Nov. 28, 2016

(86) PCT No.: PCT/EP2016/079017
§ 371 (c)(1),
(2) Date: Jun. 7, 2018

(87) PCT Pub. No.: WO2017/097624
PCT Pub. Date: Jun. 15, 2017

(65) Prior Publication Data
US 2018/0361852 A1    Dec. 20, 2018

(30) Foreign Application Priority Data

Dec. 10, 2015  (DE) .................. 10 2015 224 836

(51) Int. Cl.
*G08B 23/00*   (2006.01)
*B60K 28/06*   (2006.01)
(Continued)

(52) U.S. Cl.
CPC ............ *B60K 28/06* (2013.01); *A61B 5/0031* (2013.01); *A61B 5/076* (2013.01);
(Continued)

(58) Field of Classification Search
CPC .................................. A61N 1/37; B60K 28/06
(Continued)

(56) References Cited

U.S. PATENT DOCUMENTS 6,480,744 B2 * 11/2002 Ferek-Petric ...... A61N 1/37258
128/903
8,423,205 B2 *  4/2013 Doerr .................. A61N 1/37252
607/32
(Continued)

FOREIGN PATENT DOCUMENTS

DE    102010003191 A1    11/2010
DE    102011120510 A1    6/2012
(Continued)

OTHER PUBLICATIONS

Search Report for German Patent Application No. 10 2015 224 836.4; dated Nov. 18, 2016.
(Continued)

*Primary Examiner* — Toan N Pham
(74) *Attorney, Agent, or Firm* — Barnes & Thornburg LLP

(57) ABSTRACT

A method for controlling a functional component of a transportation vehicle by a medical implant of a user of the transportation vehicle including transmitting a signal, which comprises authentication information and status information, from the medical implant to a control device of the transportation vehicle; receiving the signal; establishing validity or invalidity of the received signal; and providing a control command to the functional component of the transportation vehicle, in the case of established validity, in
(Continued)

response to status information that indicates a critical health status of the user.

10 Claims, 3 Drawing Sheets

(51) Int. Cl.
<table>
<tr><td>G06F 19/00</td><td>(2018.01)</td></tr>
<tr><td>A61B 5/00</td><td>(2006.01)</td></tr>
<tr><td>A61B 5/07</td><td>(2006.01)</td></tr>
<tr><td>A61N 1/372</td><td>(2006.01)</td></tr>
<tr><td>A61M 5/142</td><td>(2006.01)</td></tr>
<tr><td>B60W 40/08</td><td>(2012.01)</td></tr>
<tr><td>G16H 50/30</td><td>(2018.01)</td></tr>
</table>

(52) U.S. Cl.
CPC ..... *A61M 5/14276* (2013.01); *A61N 1/37252* (2013.01); *B60W 40/08* (2013.01); *G06F 19/32* (2013.01); *A61B 2503/22* (2013.01); *A61M 2205/3576* (2013.01); *A61M 2205/50* (2013.01); *A61M 2205/502* (2013.01); *B60W 2040/0818* (2013.01); *B60W 2540/28* (2013.01); *G16H 50/30* (2018.01)

(58) Field of Classification Search
USPC ............. 340/576; 607/32, 60; 128/903, 272; 701/36, 70
See application file for complete search history.

(56) References Cited

U.S. PATENT DOCUMENTS

<table>
<tr><td>2005/0137753 A1</td><td>6/2005</td><td>Basson et al.</td></tr>
<tr><td>2008/0097550 A1</td><td>4/2008</td><td>Dicks et al.</td></tr>
<tr><td>2009/0073991 A1</td><td>3/2009</td><td>Landrum et al.</td></tr>
<tr><td>2009/0267774 A1</td><td>10/2009</td><td>Enegren et al.</td></tr>
<tr><td>2012/0023049 A1</td><td>1/2012</td><td>Doerr et al.</td></tr>
<tr><td>2013/0030645 A1</td><td>1/2013</td><td>Divine et al.</td></tr>
<tr><td>2014/0172229 A1</td><td>6/2014</td><td>Rude et al.</td></tr>
<tr><td>2014/0240132 A1</td><td>8/2014</td><td>Bychkov</td></tr>
</table>

FOREIGN PATENT DOCUMENTS

<table>
<tr><td>DE</td><td>102011016776 A1</td><td>10/2012</td></tr>
<tr><td>DE</td><td>102012002762 A1</td><td>8/2013</td></tr>
<tr><td>DE</td><td>102012014717 A1</td><td>1/2014</td></tr>
<tr><td>EP</td><td>2143468 A1</td><td>1/2010</td></tr>
<tr><td>EP</td><td>2380627 A1</td><td>10/2011</td></tr>
</table>

OTHER PUBLICATIONS

Search Report for International Patent Application No. PCT/EP2016/079017; dated Mar. 16, 2017.

* cited by examiner

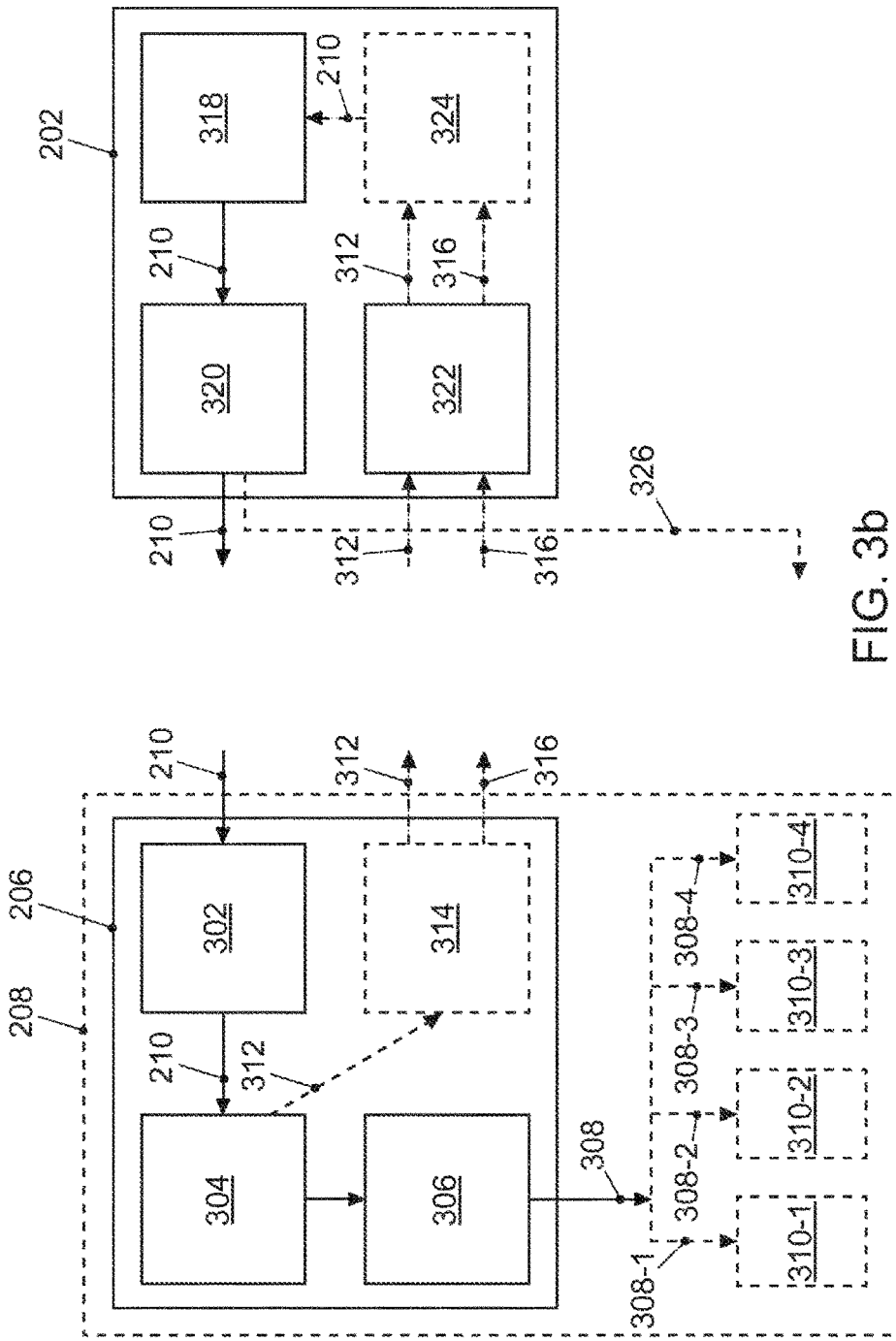

METHOD FOR CONTROLLING A FUNCTIONAL COMPONENT OF A TRANSPORTATION VEHICLE BY A MEDICAL IMPLANT OF A USER OF THE TRANSPORTATION VEHICLE, COMPUTER PROGRAM, CONTROL DEVICE FOR A TRANSPORTATION VEHICLE, AND MEDICAL IMPLANT

PRIORITY CLAIM

This patent application is a U.S. National Phase of International Patent Application No. PCT/EP2016/079017, filed 28 Nov. 2016, which claims priority to German Patent Application No. 10 2015 224 836.4, filed 10 Dec. 2015, the disclosures of which are incorporated herein by reference in their entireties.

SUMMARY

Illustrative embodiments relate to the field of the control of a functional component of a transportation vehicle by a medical implant of a user of the transportation vehicle.

BRIEF DESCRIPTION OF THE DRAWINGS

Disclosed embodiments are described and explained in more detail below with reference to the appended figures, in which, specifically:

FIG. 3a shows a block diagram of a control apparatus of a transportation vehicle according to a detailed exemplary embodiment; and FIG. 3b shows a block diagram of a medical implant according to a detailed exemplary embodiment.

DETAILED DESCRIPTION

Figure 1:
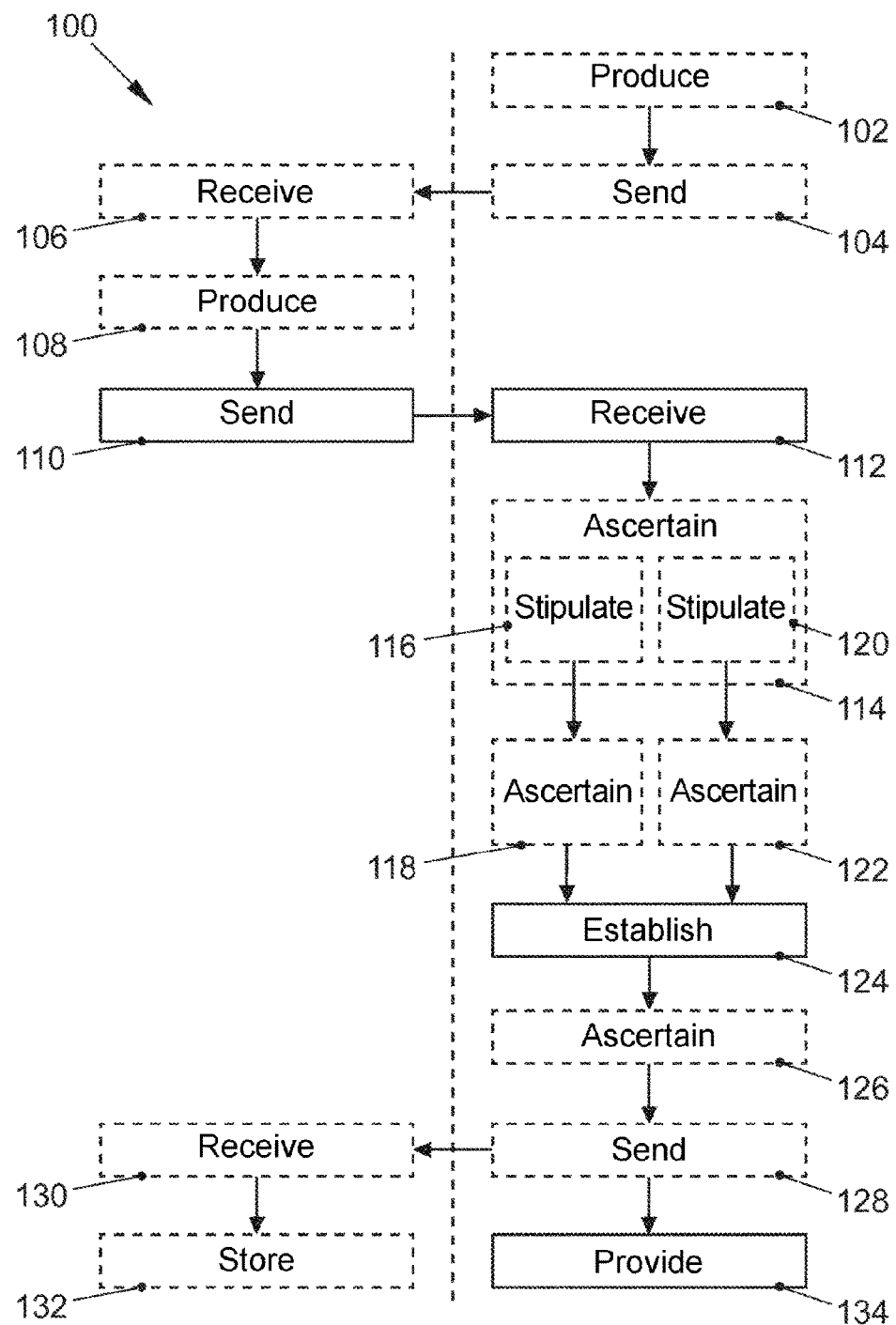
FIG. 1 shows a flowchart for a method for controlling a functional component of a transportation vehicle by a medical implant of a user of the transportation vehicle.

In medicine, patients are frequently equipped with implants, e.g., cardiac pacemakers or cardioverter defibrillators, that are capable of relieving or stopping health complaints in a patient using preventive measures. If the state of health of the patient spontaneously worsens beyond a usual degree, however, an unpleasant or even critical situation can arise for the patient that may be a hindrance in road traffic, for example. Conventional driver assistance systems can therefore undertake partial control of a transportation vehicle driven by the patient in a medical emergency of this kind. If the automobile does not detect any steering actions even though the sensors of the lane-keeping assistant detect deviation from the road, it is possible, e.g., for the driver to be warned and finally for the automobile to be brought to a controlled standstill. However, if this case arises with patients having implanted cardioverter defibrillators or cardiac pacemakers, for example, an avoidable delay can occur between detection of the medical emergency by the implant, on the one hand, and by the transportation vehicle itself, on the other. The time of the delay may possibly be physically unpleasant for the patient, or else can lead to unnecessary obstruction of further road users. Such problems can also arise, outside road traffic, in other situations in which machines are controlled or operated by implant carriers.

It is therefore desirable to improve a design for communication between a medical implant and a transportation vehicle.

Disclosed embodiments provide an apparatus, a method and a computer program.

Exemplary embodiments relate to a method for controlling a functional component of a transportation vehicle by a medical implant of a user of the transportation vehicle. The method comprises sending a signal, comprising authentication information and state information, from the medical implant to a control apparatus of the transportation vehicle. The method also comprises receiving the signal. Moreover, the method comprises establishing a validity or invalidity of the received signal. Moreover, the method comprises providing a control command, if a validity is established, as a reaction to state information indicating a critical state of health of the user, to the functional component of the transportation vehicle. Therefore, a time between the occurrence of a worsening of the state of the user, which in some cases may not be immediately perceptible to him, and detection of this state by the transportation vehicle can be shortened considerably. If need be, the transportation vehicle can even take measures immediately on the occurrence of the worsened state of health of the user to warn the user or avoid traffic obstructions. Additionally, it may be possible for the control apparatus to distinguish between an authentic signal and a false signal so as thereby to prevent, e.g., replay attacks or attacks by manipulated signals.

In some exemplary embodiments, the method further comprises ascertaining a time window for a validity of the signal based on the authentication information. Opportunities for improper applications can thus be limited considerably.

In some exemplary embodiments, the method further comprises ascertaining a time of production of the signal from the authentication information. In this case, the ascertaining of the time window comprises stipulating an end of the time window for a time no later than one minute after the time of production of the signal. This allows an up-to-dateness of the signal to be checked, and the authenticity of the signal to be established.

In some exemplary embodiments, the method further comprises ascertaining an explicit sequence of characters from the authentication information. In this case, the ascertaining of the time window comprises stipulating an end of the time window immediately after a time at which the explicit sequence of characters was received by the control apparatus for the first time. In this way, it is possible for a cryptographic secret to be made accessible only to the medical implant and the control apparatus, on the basis of which secret the authenticity of the signal can be established.

In some exemplary embodiments, the method further comprises producing the explicit sequence of characters by the control apparatus. The method moreover comprises sending the explicit sequence of characters from the control apparatus to the medical implant. The method additionally comprises receiving the explicit sequence of characters. In other words, this can mean generating the cryptographic secret on the control apparatus, as a result of which a probability of a successful eavesdropping attack can be reduced further.

In some exemplary embodiments, the method further comprises ascertaining a passenger position or a driver position at which the user is located inside the transportation vehicle based on the signal. It may thus be possible to react with different measures depending on which user of the transportation vehicle is affected.

In some exemplary embodiments, the method further comprises sending an information signal with information about a transportation vehicle state to the medical implant. This can possibly facilitate a later diagnosis for medical support personnel, since the information about the transportation vehicle state sometimes allows more accurate information to be obtained about a cause of the worsening of the state of the user.

In some exemplary embodiments, the method further comprises storing the information signal. Therefore, the information may be available not just up until a diagnosis by medical personnel, but also afterwards, for example, for statistical purposes or to inform the user, to prevent future worsenings of the state of health.

In some exemplary embodiments, the method further comprises producing the signal based on a critical state of health of a user carrying the medical implant. In this case, the signal comprises the authentication information and the state information. This allows a warning to be provided to the control apparatus, possibly immediately the worsening of the state of the user occurs, and a distinction to be drawn between a genuineness of the warning and a possible unauthorized or unwanted access.

Furthermore, further exemplary embodiments also provide a program or computer program having a program code for performing one of the cited methods when the program code is executed on a computer, a processor or a programmable hardware component, such as, e.g., an application-specific integrated circuit (ASIC).

Further exemplary embodiments relate to a control apparatus for a transportation vehicle. The control apparatus comprises a receiver configured to receive a signal from a medical implant of a user of the transportation vehicle. In this case, the signal comprises authentication information and state information. The control apparatus also comprises a checking module configured to take the authentication information as a basis for establishing a validity or invalidity of the received signal. The control apparatus additionally comprises a control device that, if a validity is established, is configured to react to state information indicating a critical state of health of the user by providing a control command to a functional component of the transportation vehicle. Therefore, a time between the occurrence of a worsening of a state of the user and the detection of this state by the transportation vehicle can be shortened considerably. If need be, the transportation vehicle can even take measures to warn the user or to avoid traffic obstructions immediately the worsened state of health of the user occurs. Additionally, it may be possible for the control apparatus to distinguish between an authentic signal and a false signal so as to prevent, e.g., replay attacks or attacks by manipulated signals.

In some exemplary embodiments, the checking module is configured to take the authentication information as a basis for ascertaining a time window, and to establish a validity of the received signal if a time of reception of the signal is inside the time window, or to establish an invalidity of the received signal if the time of reception of the signal is outside the time window. Opportunities for improper applications can thus be limited considerably.

In some exemplary embodiments, the checking module is configured to ascertain from the authentication information a time of production at which the signal was produced, and to stipulate an end of the time window for a time no longer than one minute after the time of production. This allows an up-to-dateness of the signal to be checked, and the authenticity of the signal to be established on the basis thereof.

In some exemplary embodiments, the checking module is configured to ascertain an explicit sequence of characters from the authentication information, and to stipulate an end of the time window immediately after a time at which the explicit sequence of characters was received by the receiver for the first time. In this way, it may be possible for a cryptographic secret to be made accessible only to the medical implant and the control apparatus, on the basis of which secret the authenticity of the signal can be established.

In some exemplary embodiments, the checking module is configured to produce the explicit sequence of characters. The control apparatus further comprises a transmitter configured to send the explicit sequence of characters to the medical implant. In other words, this can mean generating the cryptographic secret on the control apparatus, as a result of which a probability of a successful eavesdropping attack can be reduced further.

In some exemplary embodiments, the checking module is configured to take the signal as a basis for ascertaining a passenger position or a driver position at which the user is located inside the transportation vehicle. It may thus be possible to react with different measures depending on which user of the transportation vehicle is affected.

In some exemplary embodiments, the checking module is configured to ascertain from the authentication information an identifier explicitly associated with a passenger position or a driver position in the transportation vehicle. The identifier can be allocated when the user gets in, for example, or by a proximity sensor that registers the implant approaching a seat inside the transportation vehicle, for example. Alternatively, the identifier can be allocated by a manual user input.

In some exemplary embodiments, the checking module is configured to ascertain from the signal an origin direction and/or origin distance indicating a passenger position or a driver position in the transportation vehicle. This can be accomplished, by way of example, using known and popular methods, such as, e.g., beamforming, these being able to be implementable with comparatively low complexity.

In some exemplary embodiments, the control device is configured to use the control command to prompt slowing of an engine of the transportation vehicle or control of a steering of the transportation vehicle if the signal is associated with a medical implant of a user at the driver position. This can simplify driving of the transportation vehicle considerably for a driver having impaired health, and can thus possibly allow improved control of the transportation vehicle.

In some exemplary embodiments, the control device is configured to use the control command to prompt a visual signal output by a display device of the transportation vehicle or an audio output by a loudspeaker for the transportation vehicle if the signal is associated with a medical implant of a user at a passenger position. It is therefore possible for the user to be warned in good time about impairment of his state of health beginning, but also for any unnecessary automatic interventions in operation of the transportation vehicle to be avoided in this case.

In some exemplary embodiments, the control apparatus further comprises a transmitter configured to send an information signal with information about a transportation vehicle state to the medical implant. This can possibly facilitate a later diagnosis for medical support personnel, since the information about the transportation vehicle state sometimes allows more accurate information to be obtained about a cause of the worsening of the state of the user.

In some exemplary embodiments, the transmitter is configured to send the information signal with information comprising a transportation vehicle interior temperature, a number of kilometers most recently covered at a time and/or a travel time most recently covered at a time to the medical implant. Such parameters may be useful for a diagnosis, since they can possibly play a part in a worsening of the state of the user.

Some exemplary embodiments also relate to a transportation vehicle comprising a cited control apparatus. This allows participation in road traffic to be facilitated considerably for implant-carrying users.

Further exemplary embodiments relate to a medical implant. The medical implant comprises a signal generator configured to take a critical state of health of a user carrying the medical implant as a basis for producing a signal. The signal in this case comprises authentication information and state information. The medical implant further comprises a transmitter configured to send the signal to a control apparatus of a transportation vehicle. This sometimes allows communication with the transportation vehicle, so that the latter can become aware of a worsening of the state of health of the user more quickly. Any assistive measures can thus possibly be taken more quickly or else automatically by the control apparatus.

In some exemplary embodiments, the signal generator is configured to produce the signal with the authentication information. In this case, the authentication information comprises a time of production of the signal and/or an explicit sequence of characters. The implant can therefore be identified as the source of the signal by the control apparatus of the transportation vehicle, as a result of which it is possible for improper use or reactions to false alarms to be avoided.

In some exemplary embodiments, the medical implant further comprises a receiver. The receiver is configured to receive the explicit sequence of characters from the control apparatus. Therefore, a cryptographical secret can be agreed between the implant and the control apparatus.

In some exemplary embodiments, the medical implant further comprises a receiver configured to receive an information signal with information about a transportation vehicle state from the control apparatus. This can allow additional information that may be useful for a diagnosis to be stored on the implant.

In some exemplary embodiments, the medical implant further comprises a memory module configured to store the explicit sequence of characters or the information signal. This can possibly allow an improvement in a diagnosis.

In some exemplary embodiments, the signal generator is configured to produce an explicit identification signal. The transmitter may further be configured to send the identification signal to a functional component of the transportation vehicle. The implant can therefore possibly be used as access authorization, for example, to unlock and lock the transportation vehicle, or to start an engine of the transportation vehicle.

Various exemplary embodiments are now described in greater detail with reference to the accompanying drawings, which depict a few exemplary embodiments. In the figures, the thickness dimensions of lines, layers and/or regions may be depicted in an exaggerated state for the sake of clarity.

In the following description of the appended figures, which show exemplary embodiments, like reference symbols denote like or comparable components. Further, combinative reference symbols are used for components and objects that occur repeatedly in an exemplary embodiment or in a drawing, but are described jointly with regard to one or more features. Components or objects that are described using like or combinative reference symbols may be embodied identically, but possibly also differently, in respect of single, multiple or all features, for example, their dimensions, unless the description explicitly or implicitly reveals otherwise.

Although exemplary embodiments can be modified and altered in various ways, exemplary embodiments are depicted as examples in the figures and are described comprehensively herein. However, it should be clarified that there is no intention to restrict exemplary embodiments to the forms respectively disclosed, but rather that exemplary embodiments are intended to cover all functional and/or structural modifications, equivalents and alternatives that lie within the scope of the disclosure. Like reference symbols denote like or similar elements throughout the description of the figures.

It is noted that one element denoted as "connected" or "coupled" to another element can be directly connected or coupled to the other element or that intervening elements can be present. By contrast, if one element is denoted as "directly connected" or "directly coupled" to another element, then no intervening elements are present. Other terms used to describe the relationship between elements should be interpreted in a similar manner (e.g., "between" vis-à-vis "directly therebetween", "adjacent" vis-à-vis "directly adjacent", etc.).

The terminology used herein serves only to describe specific exemplary embodiments and is not intended to restrict the exemplary embodiments. As used herein, the singular forms "a" and "the" are also intended to include the plural forms, unless clearly indicated otherwise by the context. Further, it should be clarified that the expressions such as, e.g., "comprises", "comprising", "has" and/or "having", as used herein, indicate the presence of stated features, whole numbers, operations, work sequences, elements and/or components, but do not rule out the presence or the addition of one or more features, whole numbers, operations, work sequences, elements, components and/or groups thereof.

Unless defined otherwise, all terms used herein (including technical and scientific terms) have the same meaning that is ascribed to them by a person of average skill in the art in the field to which the exemplary embodiments belong. Further, it should be clarified that expressions, e.g., those defined in generally used dictionaries, should be interpreted as if they have the meaning that is consistent with their meaning in the context of the relevant art, and should not be interpreted in an idealized or excessively formal sense, unless this is expressly defined herein.

Patients with implants, for example, cardioverter defibrillators or cardiac pacemakers, have a precise sensor for detecting a medical emergency implanted in their own body. The sensor can allow more precise detection than, e.g., conventional driver assistance systems, which merely sense differences in a driving behavior of the patient, or user of the transportation vehicle. The exemplary embodiments below allow the decision of the transportation vehicle regarding whether the user is in a medical emergency to be made additionally on the basis of the sensor data of possible implants of the driver. An implant according to some exemplary embodiments can be read, e.g., by radio. If the implant, in the event of, e.g., ventricular fibrillation being detected, sends this information to the transportation vehicle in an integral and authentic state, a control device of the transportation vehicle can take this trustworthy information as a basis for bringing the transportation vehicle to a standstill more quickly and in a controlled state. The sensor system of a defibrillator can sometimes detect the medical emergency of the user both more quickly and more precisely. In comparison with conventional driver assistance systems, e.g., a deviation from the road would occur at a time after the ventricular fibrillation, and could thus be registered merely with a time delay. Also, a probability of error when deciding about the medical emergency of the user may be lower in the case of the implant than in the case of a lane-keeping assistant, which possibly cannot distinguish between intentional and enforced crossing of a solid line. Moreover, the present exemplary embodiments can allow patients with such implants to overcome the fear of driving an automobile.

FIG. 1 shows a flowchart for a method 100 for controlling a functional component of a transportation vehicle by a medical implant of a user of the transportation vehicle. The figure shows such method operations as take place on the implant on the left-hand side of a dashed line, and such operations as take place on the transportation vehicle, or by a control apparatus of the transportation vehicle, on the right-hand side of the dashed line. First, method operations of a simple exemplary embodiment that are depicted as solid boxes will be explained. Optional further method operations, all, some or else none of which can optionally take place in addition to those mentioned previously, are depicted as dashed boxes, and are described in even more detail subsequently.

The method 100 comprises sending 110 a signal, comprising authentication information and state information, from the medical implant to the control apparatus of the transportation vehicle. Signals may be analog or digital, continuous or discrete, periodic or aperiodic. Authentication information may be such information as allows explicit tracking of an origin of the signal, for example, over time or in space, but also in regard to a sender. This may be a signature, for example. State information can provide information about a state of health of the implant-carrying user. In a simple exemplary embodiment, this can take place digitally, for example; as such the value "low" or "0" can signify an uncritical state of health of the user and the value "high" or "1" can signify a critical state of health of the user. The control apparatus may be, e.g., an onboard computer of a transportation vehicle or a driver assistance system. A medical implant may be, e.g., a cardiac pacemaker, cardioverter defibrillator, an insulin pump, a device for deep-brain stimulation, etc.

The method 100 also comprises receiving 112 the signal. The reception 112 can be effected by a receiver on the control apparatus. Moreover, the method 100 comprises establishing 124 a validity or invalidity of the received signal by the control apparatus. Additionally, the method 100 comprises providing 134 a control command from the control apparatus, if a validity is established, as a reaction to state information indicating a critical state of health of the user, to the functional component of the transportation vehicle. Functional components can comprise, e.g., a steering, an engine, a display, an indicator lamp, a horn or a loudspeaker. A worsening of the state of the user may not be perceptible to him immediately in some cases, and the transportation vehicle can thus provide at least an indication, or even take driver-assistive measures. This can comprise the transportation vehicle being driven by the control apparatus or in a computer-aided state. Additionally, e.g., an invalidity of the signal can indicate a replay attack or false alarm. Replay attacks can take place generally by virtue of a signal being listened to by a further device, copied and reproduced at a later time that an unauthorized attacker can choose freely. This allows, e.g., deliberate stopping of transportation vehicles by an unauthorized attacker to be possibly prevented. Additionally, false alarms could, in conventional cases, possibly be triggered by routine signals that are sometimes sent from the implant to the control apparatus but comprise no state information about a critical state of health of the user. Therefore, in an exemplary embodiment, a piece of authentication information can be dispensed with for a routine signal of this kind.

In some exemplary embodiments, the method 100 further comprises ascertaining 114 a time window for a validity of the signal based on the authentication information. The time window may be limited at least backwards in this case. Therefore, a valid signal may be characterized, e.g., by a piece of authentication information meeting a condition that indicates a timing of the signal inside the time window. Conversely, a timing outside the time window can signify an invalidity of the signal.

According to a disclosed embodiment, the method 100 comprises ascertaining 118 a time of production of the signal from the authentication information. The time of production can comprise, e.g., a date and a time of day, in particular, a time of day accurate at least to the minute but optionally to the second. In this case, the ascertaining 114 of the time window comprises stipulating 116 an end of the time window for a time no later than one minute after the time of production of the signal. The time may alternatively also be at most five minutes, ten seconds or one second after the time of production. A beginning of the time window can further be stipulated for the time of production, for example. As a result, checking the authenticity of the signal or the integrity of a nonce can be used to establish the up-to-dateness or validity of the signal.

According to another disclosed embodiment, the method 100 further comprises ascertaining 122 an explicit sequence of characters from the authentication information. In this case, the ascertaining 114 of the time window comprises stipulating 120 an end of the time window immediately after a time at which the explicit sequence of characters was received by the control apparatus for the first time. In this case, such reception can relate to reception from a source outside the control apparatus. By contrast, it is possible, e.g., for a transceiver of the control apparatus to receive the explicit sequence of characters from a module of the control apparatus that generates the sequence of characters, this being able to be ignored in this case, however. The transceiver can subsequently send the sequence of characters to the medical implant. A beginning of the time window can further be stipulated for a time at which the explicit sequence of characters was received by the medical implant for the first time, for example.

The sequence of characters may be a numerator or a serial number, for example. The sequence of characters may additionally be a particular nonce or transaction number produced on a random basis and/or from a table stored on the control apparatus. The sequence of characters can lose its validity after single use; in particular, the sequence of characters can, e.g., verify the validity of a signal exclusively for the next transaction (the sending 110 and the receiving 112). The sequence of characters can depict a function of the nonce and of a cryptographic secret that is accessible only to the medical implant and the control apparatus. The validity of the signal can be verified by the sequence of characters. The time window can further begin at a time at which the implant becomes aware of the sequence of characters.

In this case, the method 100 can comprise producing 102 the explicit sequence of characters by the control apparatus. The producing 102 can, as described, be effected by a random number generator, by selecting from a preproduced table, or otherwise. In a simple exemplary embodiment, the sequence of characters can comprise a binary code, or numeric, alphanumeric and/or special characters. In a further context, the sequence of characters may also be an explicit frequency or time characteristic of an electromagnetic communication signal. In an exemplary embodiment of this kind, the method 100 moreover comprises sending 104 the explicit sequence of characters from the control apparatus to the medical implant. The method 100 moreover comprises receiving 106 the explicit sequence of characters.

In some exemplary embodiments, the method 100 further comprises producing 108 the signal based on a critical state of health of a user carrying the medical implant. In this case, the signal comprises the authentication information and the state information. The sending 110 of the signal, or in other words of a warning to the control apparatus about a worsening of the state of health of the user, can thus take place immediately the worsening of the state occurs. In this case, it is possible to distinguish between a genuineness of the warning and possible unauthorized or unintentional access.

In some exemplary embodiments, the method 100 further comprises ascertaining 126 a user position inside the transportation vehicle, based on the signal. The user position may be a passenger position in a front-seat passenger's or rear seat, or a driver position in a driver's seat, at which the user is located. By way of example, the ascertaining 126 of the user position can be performed by beamforming. An original position of the signal can be ascertained, e.g., from propagation time differences for the signal to multiple different receivers of the control apparatus. Further, it is also possible to obtain, e.g., from the signal a piece of information referenced to a position. As such, e.g., an implant-carrying user can identify himself as the driver of the transportation vehicle by manual input of the control apparatus, and alternatively or additionally a further implant-carrying user can identify himself as a passenger. As a result, it may be possible to react with different measures depending on which user of the transportation vehicle is affected.

In some exemplary embodiments, the method 100 further comprises sending 128 an information signal with information about a transportation vehicle state to the medical implant. Information about the transportation vehicle state may be, e.g., an interior temperature of the transportation vehicle (for example, at the time of reception 112 of the signal, but also over a particular period), a number of kilometers or route time most recently travelled at a time. Such information can sometimes allow more accurate information to be obtained about a cause of the worsening of the state of the user. This may possibly be useful for medical support personnel or the user himself.

Accordingly, the method 100 can comprise receiving 130 the information signal. In some exemplary embodiments, the method 100 also comprises storing 132 the information signal. Therefore, the information may be available not only up to a diagnosis by medical personnel but also afterwards, for example, for statistical purposes.

The method 100 may be able to be performed for a system comprising a medical implant and a control apparatus of a transportation vehicle. Additionally, parts of the method 100 may in themselves be further methods that are able to be performed only by the medical implant or the control apparatus. According to an exemplary embodiment, a further method for the control apparatus of the transportation vehicle comprises at least producing 102 and sending 104 the explicit sequence of characters to the medical implant. Such a method can be performed as an alternative, as a supplement or in addition to other exemplary embodiments or possibly with further method operations.

According to another exemplary embodiment, a further method for the medical implant comprises at least receiving 106 the explicit sequence of characters, producing 108 and sending 110 the signal. The producing 108 occurs in this case based on a critical state of health of the implant-carrying user, and such that the signal comprises authentication information, which in turn comprises the explicit sequence of characters. Additionally, the signal comprises state information about the state of health of the user.

According to another exemplary embodiment, a further method for the control apparatus of the transportation vehicle comprises at least receiving 112 the signal, establishing 124 the validity of the signal and providing 134 the control command, if a validity is established, to the functional component of the transportation vehicle. Alternatively, the receiving 112 can be followed by an invalidity of the signal being established, and production of a control command can be dispensed with. Optionally, the ascertaining 114 of the time window can follow the receiving 112 of the signal, and in this case comprise the stipulating 116; 120 of the end of the time window according to embodiments described above. In this case, the ascertaining 122 of the explicit sequence of characters, or alternately the ascertaining 118 of the time of production of the signal, takes place beforehand, at the same time or subsequently. On that basis, the establishing 124 of the validity of the signal and the ascertaining 126 of the position of the implant-carrying user take place. Optionally, the method comprises sending 128 the information about the transportation vehicle state to the implant.

According to yet a further exemplary embodiment, a further method for the medical implant comprises at least receiving 130 and storing 132 the information about the transportation vehicle state.

The last four mentioned exemplary embodiments of implant and control apparatus methods may each be able to be used on their own or in any combinations with one another. By way of example, the methods may be performable, and can be implemented, on processors, microcontrollers or other programmable hardware components. To this end, implementation can be performed by a computer program comprising an algorithm for performing the respective method.

Figure 2:
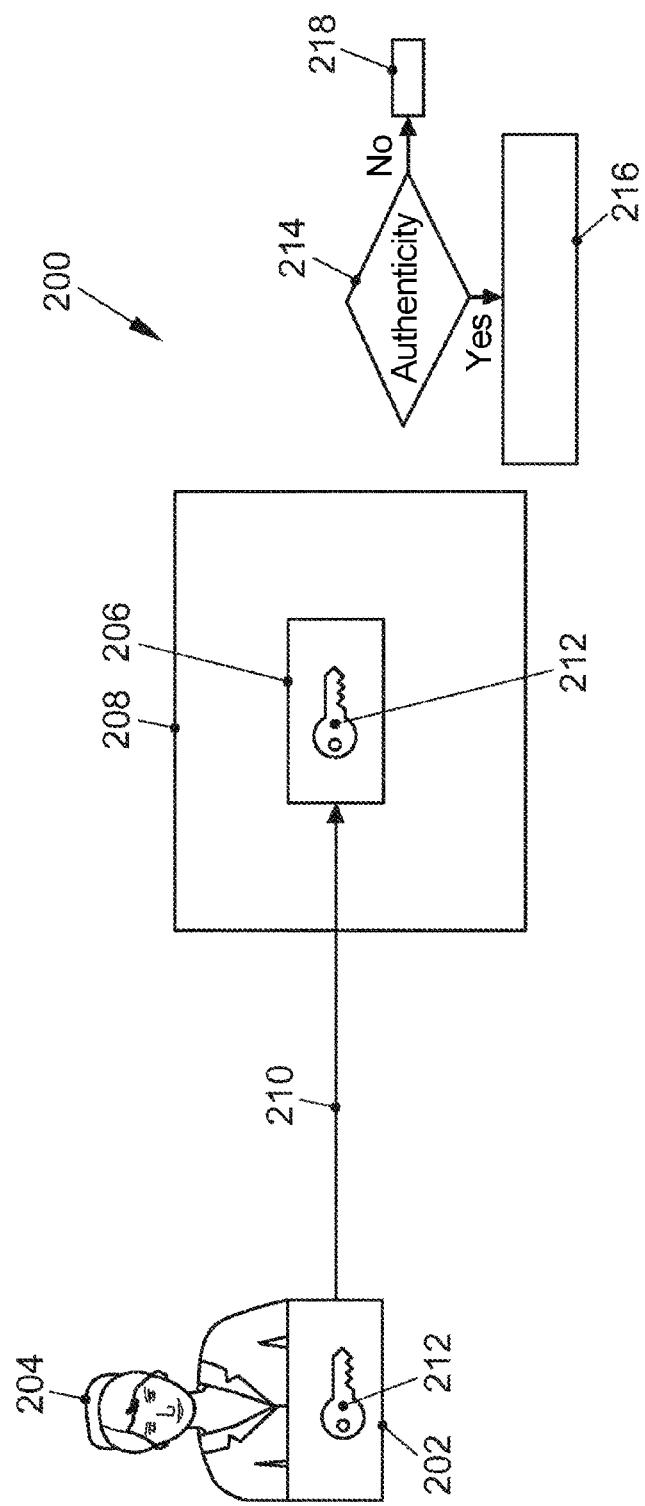
FIG. 2 shows a schematic diagram of a system comprising a medical implant and a control apparatus of a transportation vehicle and the operation thereof according to a simple exemplary embodiment.

FIG. 2 shows a simple exemplary embodiment of a system 200 comprising a medical implant 202 of a user 204 and a control apparatus 206 of a transportation vehicle 208. The implant 202 is a defibrillator or cardiac pacemaker, for example. The control apparatus 206 is a transportation vehicle computer or driver assistance system, for example. The implant 202 and the control apparatus 206 may be in contact with one another, e.g., by radio link. In a medical emergency or when the state of health of the user 204 is becoming critical, an authentic and integral report can be sent to the control apparatus 206 of the transportation vehicle 208 by radio. The report may be a signal 210 that has a piece of authentication information 212. The authentication information 212 may be a cryptographic key used by the control apparatus 206 to check 214 the authenticity or validity of the report. In the event of authenticity being ascertained, a function, e.g., controlled stopping of the transportation vehicle, is performed 216 by an algorithm suited to that purpose. In the absence of authenticity, the algorithm is terminated 218.

The transportation vehicle 208 can, in other words, share a cryptographic secret with the implant 202 of the driver 204. If the implant 202 detects a medical emergency situation, it can send an authentic and integral piece of information 210 about this by radio. The transportation vehicle 208 can listen for such radio messages during the journey. When such a message is detected, its authenticity can be verified, and the transportation vehicle 208 can be brought to a standstill immediately and in a controlled state.

FIG. 3a shows an even more detailed exemplary embodiment of a control apparatus 206 for a transportation vehicle 208. The control apparatus 206 comprises a receiver 302 configured to receive a signal 210 from a medical implant of a user of the transportation vehicle 208. The receiver 302 may be coupled to a transmitter, for example, or may be embodied together with a transmitter as a transceiver. By way of example, the receiver 302 can therefore comprise an antenna or an array comprising multiple antennas. The signal 210 comprises authentication information and state information. The control apparatus 206 also comprises a checking module 304 configured to take the authentication information as a basis for establishing a validity or invalidity of the received signal 210. The checking module 304 may be embodied, e.g., as a processor, microcontroller or other programmable hardware component. The checking module 304 can further comprise a memory for storing data, e.g., tables, algorithms or cryptographic information. The control apparatus 206 additionally comprises a control device 306 configured, if a validity is established, to react to state information indicating a critical state of health of the user by providing a control command 308 to a functional component 310 of the transportation vehicle 208. The control device 306 may be embodied in accordance with the checking module 304, or may even be embodied with the latter as a common hardware component. As such, a processor can undertake functionalities of the checking module 304 and the control device 306, for example. It may be possible for the control apparatus 206 to distinguish between an authentic signal 210 and a false signal, and thereby prevent, e.g., replay attacks. If a false or invalid signal is established, the control command 308 can be dispensed with.

By way of example, the checking module 304 is configured to take the authentication information as a basis for ascertaining a time window, and to establish a validity of the received signal 210 if a time of reception of the signal 210 is inside the time window, or to establish an invalidity of the received signal if the time of reception of the signal is outside the time window.

According to an embodiment already described in connection with FIG. 1, the checking module 304 is configured to ascertain from the authentication information a time of production at which the signal 210 was produced, and to stipulate an end of the time window for a time that is no later than five minutes, one minute, ten seconds, one second or just a fraction of a second after the time of production, for example. The checking module 304 can therefore be used to check an up-to-dateness of the signal 210.

According to a further embodiment described in connection with FIG. 1, the checking module 304 is configured to ascertain an explicit sequence of characters 312 from the authentication information, and to stipulate an end of the time window immediately after a time at which the explicit sequence of characters 312 was received by the receiver 302 for the first time. The explicit sequence of characters 312 may be a cryptographic secret that is accessible only to the medical implant and the control apparatus 206, and that can therefore be used to establish the authenticity of the signal 210.

To this end, the checking module 304 may be configured to produce the explicit sequence of characters 312. The control apparatus 206 further comprises a transmitter 314 configured to send the explicit sequence of characters 312 to the medical implant. Ideally, this could mean that the cryptographic secret is initially known only to the control apparatus 206, and can be shared with the implant, as a result of which a probability of a successful eavesdropping attack and/or replay attack can be reduced further. The transmitter 314 may be embodied as a common device together with the receiver 302, or in other words as a transceiver. Similarly, the transmitter 314 can comprise an antenna or an array of multiple antennas.

In some exemplary embodiments, the checking module 304 takes the signal 210 as a basis for ascertaining a passenger position or a driver position at which the user is located inside the transportation vehicle. By way of example, the checking module 304 may be configured to ascertain from the authentication information an identifier explicitly associated with a passenger position or a driver position in the transportation vehicle 208. The identifier can be allocated, for example, when the user gets in, by a position sensor for locating the implant in a particular seat inside the transportation vehicle 208, or by a manual user input.

Further, the checking module 304 is configured to ascertain from the signal 210 an origin direction and/or origin distance of the signal 210 indicating a passenger position or a driver position in the transportation vehicle, for example. To this end, it is possible for known and popular methods such as, e.g., beamforming to be used, for example.

Additionally, the control device 306 is configured to use the control command 308 to prompt slowing 308-1 of an engine 310-1 of the transportation vehicle 208 or control 308-2 of a steering 310-2 of the transportation vehicle 208 if the signal 210 is associated with a medical implant of a user at the driver position, for example. The transportation vehicle 208 can thus be brought to a standstill in a controlled and safe state. Optionally or alternatively, the control device 306 is configured to use the control command 308 to prompt a visual signal output 308-3 from a display device 310-3 of the transportation vehicle 208 (e.g., a screen of an infotainment system or an indicator lamp) or an audio output 308-4 from a loudspeaker 310-4 or else a horn of the transportation vehicle 208 if the signal 210 is associated with a medical implant of a user at a passenger position. It is thus possible firstly for required or assistive measures to be taken and secondly for unnecessary or even possibly traffic-obstructing measures to be avoided. Further, the state information of the signal 210 can, in a further exemplary embodiment, even provide information about a severity of the impairment of the state of health of the user. By way of example, one or more limit values can be used to grade whether the state of health requires just a break from driving for the user or even medical measures by specialist medical personnel. Accordingly, the measures described can be chosen, e.g., a driver can be asked to stop the transportation vehicle 208 by visual signal output 308-3 or audio output 308-4 if a state of exhaustion is established that does not yet require medical measures.

Optionally or alternatively, the transmitter 314 may be configured to send an information signal 316 with information about a transportation vehicle state to the medical implant. The information can comprise a transportation vehicle interior temperature, a number of kilometers most recently covered at a time and/or a travelling time most recently covered at a time. In other words, it is moreover possible for data, such as, e.g., sensor data, to be transmitted to the implant. Thus, data stored in the implant can be extended by surroundings data that were known to the automobile at the given time. By way of example, in the event of a medical emergency situation occurring, the transportation vehicle interior temperature could be safely transmitted to the implant and stored there. This could be used by a doctor for more accurate diagnosis, or else to settle insurance claims in the event of an accident.

Some exemplary embodiments also relate to the transportation vehicle 208, which comprises a cited control apparatus 206. The transportation vehicle 208 may be a land transportation vehicle, for example, a passenger transportation vehicle or truck, but also sometimes a watercraft or aircraft.

Exemplary embodiments can allow a secure radio link to be set up between the transportation vehicle 208 and the medical implant. Generally, data, e.g., the signal 210, the explicit sequence of characters 312 and the information 316 about the transportation vehicle state, can be encrypted before sending and decrypted again following reception. In this case, encryption can take place either on the transportation vehicle or on the implant.

FIG. 3b shows a more detailed exemplary embodiment of a medical implant 202. The medical implant 202 comprises a signal generator 318 configured to take a critical state of health of a user carrying the medical implant 202 as a basis for producing the signal 210. The signal 210 in this case comprises the authentication information and state information. The medical implant 202 further comprises a transmitter 320 configured to send the signal 210 to the control apparatus 206 of the transportation vehicle 208 (cf. FIG. 3a).

In some exemplary embodiments, in which the signal generator 318 produces the signal 210 with the authentication information, the authentication information comprises the time of production of the signal 210 and/or the explicit sequence of characters 312. The implant 202 can therefore be identified as the source of the signal 210 by the control apparatus 206 of the transportation vehicle 208, as a result of which it is possible for improper use or reactions to false alarms to be avoided.

Further, the medical implant 202 can have a receiver 322. The transmitter 320 and the receiver 322 of the medical implant 202 may in turn be configured as a common transceiver, and comprise one or more antennas, for example. The receiver 322 is configured to receive the explicit sequence of characters 312 from the control apparatus 206. Optionally, the implant 202 may be configured to transmit confirmation of reception of the explicit sequence of characters 312 to the control apparatus 206.

Furthermore, the receiver 322 may be configured to receive the information signal 316 with information about the transportation vehicle state from the control apparatus 206. Also, the medical implant can further comprise a memory module 324 configured to store the explicit sequence of characters 312 or the information signal 316.

In some exemplary embodiments, the signal generator 324 is configured to produce an explicit identification signal 326. The transmitter 320 may further be configured to send the identification signal 326 to a functional component 310 of the transportation vehicle 208. The implant 202 can therefore possibly be used as access authorization, for example, to unlock and lock the transportation vehicle 208, or to start an engine 310-1 of the transportation vehicle 208. Access to the transportation vehicle 208 can even be denied if the implant 202 has established that there is too much alcohol in the blood after valid authentication, for example. Besides actuating transportation vehicle functions, it is also possible for data to be transmitted from the implant 202 to the transportation vehicle 208 for further processing.

Exemplary embodiments can additionally also be used in future transportation vehicles for which a system is implemented that is configured to bring the transportation vehicle to a standstill in a controlled state. In this case, the transportation vehicle can support a radio process of the implant. Secure communication by an implant with other entities by radio can be transferred to other areas beyond transportation vehicle-based applications. It is thus possible for an implant to be used as access authorization, for example. This access authorization can firstly be obtained by proof of identity with a cryptographic secret. Furthermore, arbitrary further preconditions can be linked to access. By way of example, a precondition for opening a safe door may be that the implant finds a heartbeat and the rate is in a particular range.

The features disclosed in the description above, the claims below and the appended figures can be of importance and implemented both individually and in any desired combination for the realization of an exemplary embodiment in its various refinements.

Although some embodiments have been described in connection with an apparatus, it goes without saying that these embodiments also represent a description of the corresponding method, such that a block or a component of an apparatus should also be understood as a corresponding method operation or as a feature of a method operation. Analogously to this, embodiments described in connection with or as a method operation also represent a description of a corresponding block or detail or feature of a corresponding apparatus.

Depending on specific implementation requirements, exemplary embodiments can be implemented in hardware or in software. The implementation can be carried out using a digital storage medium, for example, a floppy disk, a DVD, a Blu-Ray disk, a CD, a ROM, a PROM, an EPROM, an EEPROM or a Flash memory, a hard disk or some other magnetic or optical storage device on which are stored electronically readable control signals that can interact or do interact with a programmable hardware component such that the respective method is performed.

A programmable hardware component can be formed by a processor, a central processing unit (CPU), a graphics processing unit (GPU), a computer, a computer system, an application-specific integrated circuit (ASIC), an integrated circuit (IC), a system on chip (SOC), a programmable logic element or a field programmable gate array having a microprocessor (FPGA).

The digital storage medium may therefore be machine-readable or computer-readable. Some exemplary embodiments thus comprise a data storage medium that has electronically readable control signals that are able to interact with a programmable computer program or a programmable hardware component such that one of the methods described herein is performed. At least one exemplary embodiment is therefore a data storage medium (or a digital storage medium or a computer-readable medium) on which the program for performing one of the methods described herein is recorded.

Generally, exemplary embodiments may be implemented as a program, firmware, computer program or computer program product comprising a program code or as data, wherein the program code or the data is or are operative to the effect of performing one of the methods when the program runs on a processor or a programmable hardware component. The program code or the data may, by way of example, also be stored on a machine-readable medium or data storage medium. The program code or the data may be present inter alia as source code, machine code or byte code and as other intermediate code.

A further exemplary embodiment is further a data stream, a signal train or a sequence of signals that represents or represent the program for performing one of the methods described herein. The data stream, the signal train or the sequence of signals may, by way of example, be configured to the effect of being transferred via a data communication link, for example, via the Internet or another network. Exemplary embodiments are thus also data-representing signal trains that are suitable for sending via a network or a data communication link, wherein the data represent the program.

A program according to at least one exemplary embodiment can implement one of the methods while it is being performed, for example, by reading memory locations or writing a datum or multiple data thereto, as a result of which, if appropriate, switching processes or other processes are brought about in transistor structures, in amplifier structures or in other electrical components, optical components, magnetic components or components that operate according to another functional principle. Accordingly, by a memory location being read, it is possible for data, values, sensor values or other information to be captured, determined or measured by a program. Therefore, by reading one or more memory locations, a program can capture, determine or measure variables, values, measured variables and other information and, by writing to one or more memory locations, the program can bring about, prompt or perform an action and actuate other devices, machines and components.

The exemplary embodiments described above are merely an illustration of the principles of the present disclosure. It goes without saying that modifications and variations of the arrangements and details described herein will become apparent to other persons skilled in the art. Therefore, the intention is for the disclosure to be restricted only by the scope of the protection of the patent claims below, and not by the specific details presented herein on the basis of the description and the explanation of the exemplary embodiments.

LIST OF REFERENCE SYMBOLS

100 Method
102 Produce (an explicit sequence of characters)
104 Send (the explicit sequence of characters)
106 Receive (the explicit sequence of characters)
108 Produce (a signal)
110 Send (the signal)
112 Receive (the signal)
114 Ascertain (a time window for a validity of the signal)
116 Stipulate (an end of the time window)
118 Ascertain (a time of production of the signal)
120 Stipulate (an end of the time window)
122 Ascertain (an explicit sequence of characters)
124 Establish (a validity or invalidity of the signal)
126 Ascertain (a user position inside the transportation vehicle)
128 Send (an information signal)
130 Receive (the information signal)
132 Store (the information signal)
134 Provide (a control command)
200 System
202 Medical implant
204 User
206 Control apparatus
208 Transportation vehicle
210 Signal
212 Authentication information
214 Check
216 Perform
218 Terminate
302 Receiver
304 Checking module
306 Control device
308 Control command
308-1 Slow
308-2 Control
308-3 Visual signal output
308-4 Audio output
310 Functional component
310-1 Engine
310-2 Steering
310-3 Display device
310-4 Loudspeaker
312 Explicit sequence of characters
314 Transmitter
316 Information signal
318 Signal generator
320 Transmitter
322 Receiver
324 Memory module
326 Identification signal

The invention claimed is:

1. A method for controlling a functional component of a transportation vehicle by a medical implant of a user of the transportation vehicle, the method comprising:
sending a signal from the medical implant to a control apparatus of the transportation vehicle comprising authentication information and state information;
receiving the signal;
establishing a validity or invalidity of the received signal including ascertaining a time window for the validity of the signal based on the authentication information and ascertaining:
a time of production of the signal from the authentication information; or
an explicit sequence of characters from the authentication information;
and providing a control command to the functional component of the transportation vehicle as a reaction to state information indicating a critical state of health of the user in response to validity of the critical state of the health of the user being established.

2. The method of claim 1,
wherein the ascertaining of the time window comprises stipulating an end of the time window for a time no later than one minute after the time of production of the signal.

3. The method of claim 1, wherein the ascertaining of the time window comprises stipulating an end of the time window directly after a time at which the explicit sequence of characters was received by the control apparatus for the first time.

4. The method of claim 1, further comprising ascertaining a passenger position or a driver position at which the user is located inside the transportation vehicle based on the signal.

5. The method of claim 1, further comprising sending an information signal with information about a transportation vehicle state to the medical implant.

6. The method of claim 5, further comprising storing the information signal.

7. The method of claim 1, further comprising producing the signal based on a critical state of health of the user carrying the medical implant, wherein the signal comprises the authentication information and the state information.

8. The method of claim 3, further comprising at least one of producing the explicit sequence of characters by the control apparatus, sending the explicit sequence of characters from the control apparatus to the medical implant, and/orand receiving the explicit sequence of characters.

9. A control apparatus for a transportation vehicle, the control apparatus comprising:
- a receiver to receive a signal from a medical implant of a user of the transportation vehicle, wherein the signal comprises authentication information and state information;
- a checking module to take the authentication information as a basis for establishing a validity or invalidity of the received signal; and
- a control device that reacts to state information indicating a critical state of health of the user by providing a control command to a functional component of the transportation vehicle in response to the validity of the critical state of health of the user being established, wherein the checking module takes the authentication information as a basis for ascertaining a time window, and establishes the validity of the received signal if a time of reception of the signal is inside the time window, or establishes the invalidity of the received signal if the time of reception of the signal is outside the time window.

10. A medical implant, comprising:
- a signal generator to take a critical state of health of a user carrying the medical implant as a basis for producing a signal, wherein the signal comprises authentication information and state information; and
- a transmitter to send the signal to a control apparatus of a transportation vehicle, wherein the signal generator produces the signal with the authentication information, and the authentication information comprises at least one of a time of production of the signal and an explicit sequence of characters.

* * * * *